(12) United States Patent
Vitek et al.

(10) Patent No.: US 7,377,900 B2
(45) Date of Patent: May 27, 2008

(54) ENDO-CAVITY FOCUSED ULTRASOUND TRANSDUCER

(75) Inventors: Shuki Vitek, Haifa (IL); Doron Kopelman, Cesarea (IL); Yoav Medan, Haifa (IL); Dov Maor, Haifa (IL)

(73) Assignee: Insightec - Image Guided Treatment Ltd. (IL)

( * ) Notice: Subject to any disclaimer, the term of this patent is extended or adjusted under 35 U.S.C. 154(b) by 93 days.

(21) Appl. No.: 10/452,061

(22) Filed: Jun. 2, 2003

(65) Prior Publication Data

US 2004/0242999 A1 Dec. 2, 2004

(51) Int. Cl.
*A61B 8/00* (2006.01)
*A61H 1/00* (2006.01)

(52) U.S. Cl. ............................ 600/439; 600/459; 601/3

(58) Field of Classification Search ............... 600/439, 600/459, 471; 601/2–4; 606/1; 604/22
See application file for complete search history.

(56) References Cited

U.S. PATENT DOCUMENTS

| | | | |
|---|---|---|---|
| 5,307,816 A * | 5/1994 | Hashimoto et al. ......... 600/439 |
| 5,391,140 A | 2/1995 | Schaetzle et al. |
| 5,474,071 A * | 12/1995 | Chapelon et al. ........... 600/439 |
| 5,605,154 A | 2/1997 | Ries et al. |
| 5,666,954 A | 9/1997 | Chapelon et al. |
| 5,687,729 A | 11/1997 | Schaetzle et al. |
| 5,759,162 A | 6/1998 | Oppelt et al. |
| 5,810,008 A * | 9/1998 | Dekel et al. ................ 600/443 |
| 6,004,269 A * | 12/1999 | Crowley et al. ............ 600/439 |
| 6,461,314 B1 * | 10/2002 | Pant et al. ..................... 601/2 |
| 6,679,855 B2 * | 1/2004 | Horn et al. ..................... 601/2 |
| 6,733,450 B1 * | 5/2004 | Alexandrov et al. ........ 600/439 |
| 2003/0004439 A1 | 1/2003 | Pant et al. |
| 2003/0060820 A1 | 3/2003 | Maguire et al. |

OTHER PUBLICATIONS

PCT International Search Report for PCT/IB2004/001498, Applicant: Scimed Life Systems, Inc., Forms PCT/ISA/210 and 220, dated Aug. 31, 2004 (7 pages).
PCT Written Opinion of the International Search Authority for PCT/IB2004/001498, Applicant: Scimed Life Systems, Inc., Form-PCT/ISA/237, dated Aug. 31, 2004 (5 pages).

(Continued)

*Primary Examiner*—Francis J. Jaworski
(74) *Attorney, Agent, or Firm*—Vista IP Law Group LLP

(57) ABSTRACT

An apparatus for delivering acoustic energy to a target site adjacent a body passage includes first and second elongate members, each carrying one or more transducer elements on their distal ends. The first and/or second elongate members include connectors for securing the first and second elongate members together such that the transducer elements together define a transducer array. The first and second elongate members are introduced sequentially into a body passage until the transducer elements are disposed adjacent a target site. Acoustic energy is delivered from the transducer elements to the target site to treat tissue therein. In another embodiment, the apparatus includes a tubular member and an expandable structure carrying a plurality of transducer elements. The structure is expanded between a contracted configuration during delivery and an enlarged configuration when deployed for delivering acoustic energy to a target site adjacent the body passage.

22 Claims, 5 Drawing Sheets

OTHER PUBLICATIONS

"How is the Ablatherm Treatment Performed?" http://www.edap-hifu.com/eng/physicians/hifu/3c_treatment_treat-description.htm, Jan. 3, 2003, pp. 1-3.

"What is HIFU? HIFU: High Intensity Focused Ultrasound" http://www.edap-hifu.com/eng/physicians/hifu/2a_hifu_overview.htm, Jan. 3, 2003, p. 1.

"What are the Physical Principles" http://www.edap-hifu.com/eng/physicians/hifu/2c_hifu_physical.htm, Jan. 3, 2003, pp. 1-2.

"How does HIFU Creat a Lesion?" http://www.edap-hifu.com/eng/physicians/hifu/2d_hifu_lesion.htm, Jan. 3, 2003, p. 1.

"Prostate Cancer Phase I Clinical Trials Using High Intensity Focused Ultrasound (HIFU)" *Focus Surgery*, http:/www.focus-surgery.com/PCT%20Treatment%20with%20HIFU.htm, Jan. 3, 2003, pp. 1-2.

"Abstract" *Focus Surgery*, http://www.focus-surgery.com/Sanghvi.htm, Jan. 3, 2003, p. 1.

* cited by examiner

ENDO-CAVITY FOCUSED ULTRASOUND TRANSDUCER

FIELD OF THE INVENTION

The present invention relates generally to apparatus and methods for delivering acoustic energy, and more particularly to apparatus and methods for delivering diagnostic and/or therapeutic ultrasonic energy from a transducer disposed within a body of a subject.

BACKGROUND

Devices and systems using acoustic energy, particularly within the ultrasonic range (acoustic waves with a frequency greater than about twenty kilohertz (20 kHz), and more typically between fifty kilohertz and five Megahertz (0.05-5 MHz)), have been used to diagnose and treat patients. For example, ultrasonic energy may be employed to obtain images of a region of a patient during a diagnostic or therapeutic procedure. In addition, ultrasound systems have been used for treating tissue, e.g., by focusing acoustic energy towards a target tissue region within a patient, such as a cancerous or benign tumor, to necrose or otherwise heat the tissue region. For example, one or more piezoelectric transducers may be disposed adjacent a patient's body and used to deliver high intensity acoustic waves, such as ultrasonic waves, to an internal tissue region of a patient to treat the tissue region. An exemplary focused ultrasound ("FUS") system is disclosed in U.S. Pat. No. 4,865,042 issued to Umemura et al.

Focused ultrasound procedures may allow a patient to be treated without requiring invasive surgery. Because ultrasonic transducers are generally disposed adjacent to the patient, however, the acoustic path to a target tissue region may be at least partially obstructed, e.g., by anatomical objects such as bones or cavities, within the patient's body. Furthermore, acoustic energy may not be adequately focused at a location deep within a body, e.g., because the resulting focal zone may be too large to provide an effective and safe treatment. As such, it is preferable to place the transducer as close to a target site as possible.

To deliver acoustic energy to locations deep within the body, it has been suggested to use natural body passages to place an acoustic transducer closer to a target site. For example, U.S. Pat. No. 5,666,954 discloses a transducer that may be inserted into the rectal canal through the rectal orifice to treat prostate cancer. Natural body passages, however, may limit the size of the transducer that may be introduced.

Generally, a relatively large transducer provides better control over the size and intensity of the resulting focal zone. The size of a transducer that may be delivered inside a body passage may be limited by the size of a body orifice at the entry point for the transducer. For example, the size of a transducer used for treating prostate cancer may be limited by the maximum perimeter of the rectal orifice.

Accordingly, apparatus and methods for delivering acoustic energy within a patient's body would be useful.

SUMMARY OF THE INVENTION

The present invention is directed to apparatus, systems, and methods for delivering diagnostic and/or therapeutic ultrasound energy to tissue within a subject. More particularly, the present invention is directed to apparatus and methods for delivering acoustic energy to target regions within a patient using a transducer device introduced into a body passage of the patient.

In one embodiment, an apparatus for delivering acoustic energy may include a first structure carrying a first transducer, and a second structure carrying a second transducer. The first and second transducers may be disposable adjacent one another such that together they at least partially define a transducer array. In one embodiment, the first transducer may be configured to mate with the second transducer such that together they form at least a part of the transducer array. For example, a connector or other mechanism may be provided for securing the first structure to the second structure. The apparatus may include one or more additional structures, each carrying a transducer that further defines the transducer array. Each transducer of the apparatus may include a single transducer element, although preferably, each transducer includes a plurality of transducer elements. In addition, the apparatus may include a balloon, bag, or other coupling membrane that may receive the first and second structures or otherwise may surround the resulting transducer array for acoustically coupling the transducer array with surrounding tissue.

In accordance with another aspect of the present invention, an apparatus is provided for delivering acoustic energy that includes an expandable structure carrying a plurality of transducer elements. The structure may be movable into a contracted or low profile configuration to facilitate advancing the structure into a body passage, and may be expandable to an enlarged configuration such that the plurality of transducer elements define a transducer array Optionally, the apparatus may include a tubular delivery device having a proximal end, a distal end, and a lumen extending between the proximal and distal ends. The structure may be disposed within the lumen in the contracted configuration during delivery and may be expanded to the enlarged configuration when advanced from the lumen. The apparatus may also include a balloon, bag, or other coupling membrane, similar to the previous embodiment.

In accordance with yet another aspect of the present invention, an apparatus is provided for delivering acoustic energy to a target site adjacent a body passage that includes a first member including a proximal end, a distal having a size and shape for insertion into a body passage, and a first transducer carried on the distal end. The apparatus also includes a second member also including a proximal end, a distal having a size and shape for insertion into the body passage, and a second transducer carried on the distal end. The first and/or second members include one or more connectors for substantially securing the first and second members relative to one another such that the first and second transducers together at least partially define a transducer array.

In accordance with still another aspect of the present invention, a method is provided for delivering acoustic energy into a target tissue region adjacent a body passage. A first member is introduced into a body passage until a first transducer carried by the first member is disposed adjacent the target tissue region. A second member is introduced into the body passage until a second transducer carried by the second member is disposed adjacent the first transducer. Acoustic energy is delivered from the first and second transducers towards the target tissue region to treat tissue therein.

In accordance with yet another aspect of the present invention, an apparatus is provided for delivering acoustic energy to a target region adjacent a body passage that includes a tubular member including a proximal end, a distal end having a size and shape for insertion into a body passage, and a lumen extending between the proximal and distal ends, and a structure carrying a plurality of transducer elements, the structure being movable between a contracted configuration when disposed within the lumen of the tubular member, and an enlarged configuration when deployed from the lumen such that the plurality of transducer elements at least partially define a transducer array for delivering acoustic energy to a target region adjacent the body passage.

In accordance with still another aspect of the present invention, a method is provided for delivering acoustic energy into a target tissue region adjacent a body passage. An expandable structure is introduced into a body passage while in a contracted configuration, the expandable structure carrying a plurality of transducer elements. The expandable structure is expanded towards an enlarged configuration, thereby arranging the plurality of transducer elements into an array. Acoustic energy is delivered from the plurality of transducer elements towards the target tissue region.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

DETAILED DESCRIPTION OF THE PREFERRED EMBODIMENTS

Figure 1:
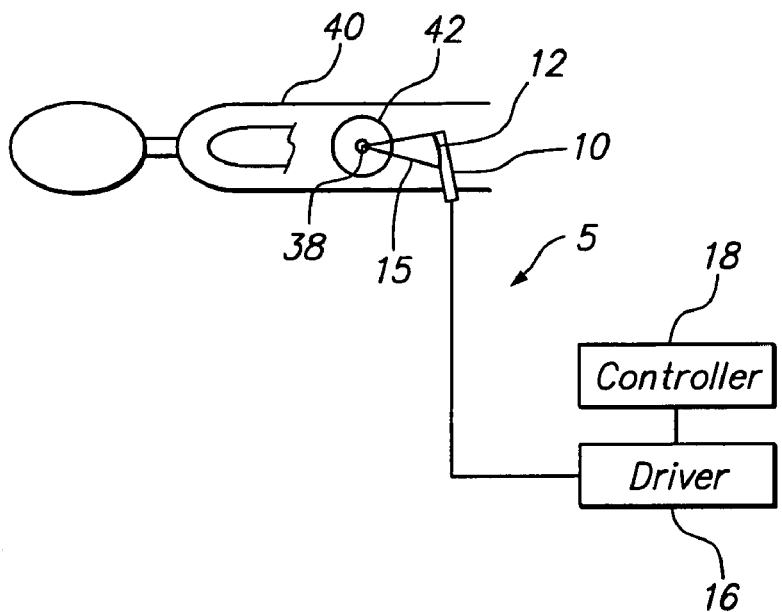
FIG. 1 shows an exemplary ultrasound system including a transducer device delivering acoustic energy to a target tissue region within a patient.

Turning to the drawings, FIG. 1 shows an exemplary embodiment of a focused ultrasound system 5 including a transducer device 10, drive circuitry 16 coupled to the transducer device 10, and a controller 18 coupled to the drive circuitry 16. As shown, the transducer device 10 generally may be introduced into a body passage 92 within a patient 90 and used to deliver acoustic energy (represented by beam 15) to a target tissue region 94 located adjacent the body passage 92. The acoustic energy 15 may be used to necrose, heat, or otherwise treat the target tissue region 94, which may be a benign or malignant tumor within an organ or other tissue structure (not shown).

The transducer device 10 generally includes one or more transducers 12 that are coupled to the driver 16 and/or controller 18 for generating and/or controlling the acoustic energy emitted by the transducer 12. For example, the driver 16 may generate one or more electronic drive signals, which may be controlled by the controller 18. The transducer 12 converts the drive signals into acoustic energy 15, which may be focused using conventional methods.

The controller 18 and/or driver 16 may be separate or integral components. It will be appreciated by one skilled in the art that the operations performed by the controller 18 and/or driver 16 may be performed by one or more controllers, processors, and/or other electronic components, including software and/or hardware components. The terms controller and control circuitry may be used herein interchangeably, and the terms driver and drive circuitry may be used herein interchangeably.

The driver 16, which may be an electric oscillator, may generate drive signals in the ultrasound frequency spectrum, e.g., as low as twenty kilohertz (20 kHz), and typically ranging from about half to ten Megahertz (0.5 to 10 MHz). Preferably, the driver 16 provides drive signals to the transducer 12 at radio frequencies (RF), for example, between about half to ten Megahertz (0.5-10 MHz), and more preferably between about one and two Megahertz (1.5 and 2.5 MHz). When the drive signals are provided to the transducer 12, the transducer 12 emits acoustic energy 15 from its exposed surface, as is well known to those skilled in the art.

The controller 18 may control the amplitude, and therefore the intensity or power of the acoustic waves transmitted by the transducer 12. The controller 18 may also control a phase component of the drive signals to respective transducer elements of the transducer 12, e.g., to control a shape of a focal zone 38 generated by the transducer 12 and/or to move the focal zone 38 to a desired location. For example, the controller 18 may control the phase shift of the drive signals based upon a radial position of respective transducer elements of the transducer 12, e.g., to adjust a focal distance of the focal plane (i.e., the distance from the face of the transducer 12 to the center of the focal zone). In addition or alternatively, the controller 18 may control the phase shift of the drive signals based upon a angular position around the face of the transducer device, e.g., to adjust a shape of the focal zone, as is well known to those skilled in the art. In addition or alternatively, the transducer 12 may be pivotable and the controller 18 may control one or more tilt angles of the transducer 12.

As explained above, the transducer 12 converts the drive signals into acoustic energy represented by energy beam 15. As the acoustic energy 15 passes through the patient's body, the acoustic energy 15 is converted to heat at the focal zone within target region 94, thereby raising the temperature of tissue within the target region 94. The acoustic energy 15 may be focused on the target region 94 to raise the temperature of the tissue to necrose the tissue within the target region 94 while minimizing damage to surrounding healthy tissue. Exemplary apparatus for measuring and/or calibrating the energy output of a transducer device are described in U.S. Pat. No. 6,790,180. The disclosure of this application and any references cited therein are expressly incorporated herein by reference.

Figure 2:
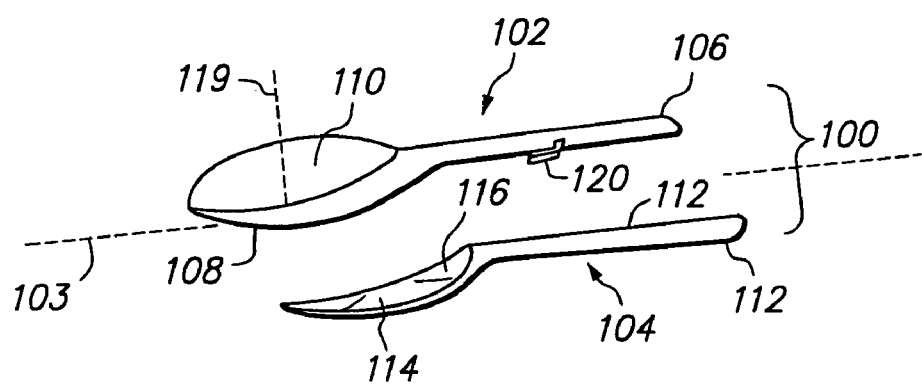
FIG. 2 is a perspective view of a first preferred embodiment of a transducer device, including first and second elongate members carrying transducer elements, that may be used in the system of FIG. 1.

Turning to FIG. 2, a first embodiment of a transducer device 100 is shown that includes a first structure or elongate member 102 and a second structure or elongate member 104. The first elongate member 102 includes a proximal end 106, a distal end 108, and one or more transducer elements 110 carried on the distal end 108. The second elongate member 104 also includes a proximal end 112, a distal end 114, and one or more transducer elements 116 carried on the distal end 114. The first and second elongate members 102, 104 may be substantially rigid, semi-rigid, or substantially flexible, preferably having sufficient column strength such that the distal ends 108, 114 may be advanced into a body passage from the proximal ends 106, 112 without substantially buckling or kinking.

Figure 3:
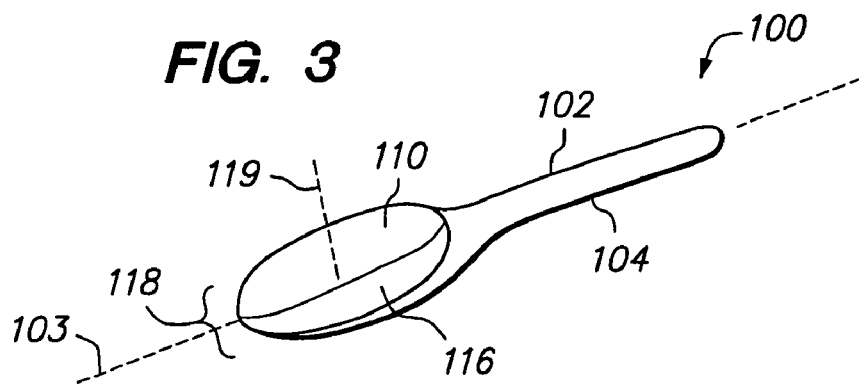
FIG. 3 is a perspective view of the transducer device of FIG. 2, showing the first and second elongate members mated together such that the transducer elements define a transducer array.

As shown in FIG. 3, the first and second elongate members 102, 104 may be mated together such that the transducer elements 110, 116 together provide a transducer array 118. Preferably, the first and second elongate members 102, 104 include cooperating connectors that may removably secure them together. For example, a hook or tab 120 may be provided on the first elongate member 102 that may be received in a corresponding opening or slot 122 (shown in phantom) in the second elongate member 104, as shown in FIG. 2. Alternatively, other connectors or locking mechanisms may be provided, as will be appreciated by those skilled in the art. For example, a snap-fit or compression-fit mechanism, cooperating slots and/or tabs for sliding engagement, and the like (not shown) may be provided for detachably securing the first and the second elongate members 102, 104 to one another.

Each of the elongate members 102, 104 has a cross-sectional dimension or width that allows the distal ends 108, 114 to be inserted into a body passage (not shown). The body passage may be a natural passage, such as a rectal orifice, mouth, esophagus, a nasal orifice, vagina, blood vessel, and the like. Alternatively, the body passage may be a surgically-created passage, e.g., as created using an endoscopic or laparoscopic instrument (not shown). As such, the cross-sectional dimension of each of the elongate members 102, 104 may vary depending upon the particular application or surgical procedure. Generally, the elongate members 102, 104 may be inserted through an initial, relatively narrow orifice into a body passage or cavity having a larger size. Thus, the initial orifice may be the limiting factor dictating the maximum cross-sectional dimension or width of the individual elongate members.

In one embodiment, the distal end 108, 116 of each of the elongate members 102, 104 has a cross-sectional dimension that is sufficiently small to allow the respective distal end 108, 114 to be inserted individually through a rectal orifice (not shown). Once inserted through the rectal orifice, the rectum or colon may provide greater space, e.g., such that the distal ends 108, 114 may be assembled together. In this example, the width or cross-sectional dimension for the distal ends 108, 116 may be between about ten and seventy millimeters (10-70 mm).

In a preferred embodiment, the elongate members 102, 104 are substantially symmetrical and have similar widths, as shown in FIGS. 2 and 3. In alternative embodiments, the elongate members 102, 104 may have different dimensions and/or may be asymmetrical relative to each other. In further alternatives, one or more additional elongate members (not shown) may be provided that include one or more transducer elements such that the transducer device may include three or more elongate members (not shown). Thus, the first and second members may be divided into two or more additional elongate members, depending upon the desired maximum cross-section of each individual elongate member, i.e., depending upon the relative size of the assembled transducer array and the orifice through which the components must pass into the body.

The elongate members 102, 104 may be made from a variety of materials, such as plastics, polymers, metals, and alloys. In the illustrated embodiment, each of the elongate members 102, 104 has an elongated body. However, the elongate members 102, 104 may have other shapes and forms so long as they are capable of providing a platform or area for carrying the respective transducer elements 110, 116.

Each of the transducer elements 110, 116 may be a one-piece piezoceramic element, or alternatively, a mosaic arrangement including a plurality of small piezoceramic elements. The piezoceramic element(s) may have a variety of geometric shapes, such as hexagons, triangles, squares, and the like, and may be disposed about a central axis 119 of the elongate members 102, 104. In a preferred embodiment, the central axis 119 may be located on the distal ends 108, 114 at a junction between the first and second elongate members 102, 104. More preferably, the transducer elements 110, 116 are arranged on the distal ends 108, 114 in a substantially uniform or symmetrical configuration about the central axis 119.

In addition, the elongate members 102, 104 may include one or more leads, e.g., wires or conductive paths (not shown), extending between the proximal ends 106, 112 and distal ends 108, 114, and coupled to the transducer elements 110, 116. The proximal ends 106, 112 may include connectors (not shown) for connecting cables and the like to the elongate members 102, 104, e.g., to couple the transducer elements 110, 116 to a driver 16 and/or controller 18 (not shown, see FIG. 1). Thus, the driver 16 and/or controller 18 may generate drive signals for causing the transducer elements 110 and 114 to emit acoustic energy. In an alternative embodiment, each of the elongate members 102, 104 may be coupled to a separate driver (not shown) that is connected to a common or separate controller(s). In yet another alternative embodiment, one of the elongate members 102, 104 may be coupled to a driver, and the other of the elongate member 102, 104 may be coupled to leads in the first elongate member when the elongate members 102, 104 are connected to one another.

As shown in FIG. 3, once the transducer device 100 is assembled, the transducer elements 110, 116 define an assembled transducer array 118. The transducer array 118 may have a variety of shapes and configurations. In one embodiment, the transducer array 118 may have a concave or bowl shape, such as a "spherical cap" shape, i.e., having a substantially constant radius of curvature such that the transducer array 118 has an inside surface defining a portion of a sphere.

Alternatively, the transducer array 118 may have a substantially flat configuration (not shown), and/or may include an outer perimeter that is generally, but not necessarily, circular (not shown). The transducer array 118 may be divided into any desired number of rings and/or sectors (not shown). In one embodiment, the transducer array 118 may have an outer diameter of between about thirty and seventy millimeters (30-70 mm), a radius of curvature between about thirty and fifty millimeters (30-50 mm), and may include between about forty and five hundred elements. For example, the transducer array 118 may be divided into between about ten and thirty (10-30) rings and about four and sixteen (4-16) sectors, although the transducer array 118 is not limited to such a configuration.

The assembled transducer array 118 may also have other configurations, such as flat circular arrays, linear arrays, and the like, so long as it may be detachably assembled from the transducer elements 110, 114 carried by multiple structures, such as the elongate members 102, 104. The transducer array 118 may be arranged generally in a plane that is substantially parallel to the longitudinal axis 103 of the elongate members 102, 104, or the array 1118 may be oriented at an angle with respect to the longitudinal axis 103. Additional information on the construction and use of transducer arrays may be found in co-pending application Ser. No. 09/884,206, filed Jun. 19, 2000. The disclosure of this application and any references cited therein are expressly incorporated herein by reference.

Figure 4:
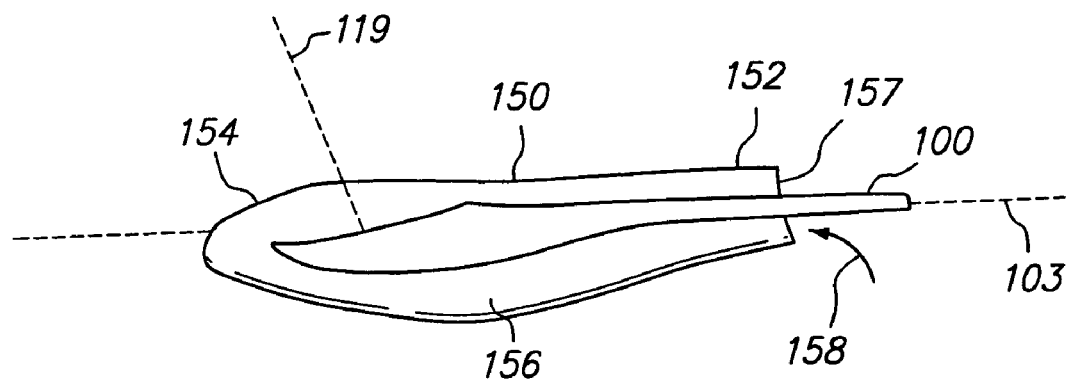
FIG. 4 is a cross-sectional side view of an alternative embodiment of the transducer device of FIGS. 2 and 3, including an expandable balloon surrounding the transducer elements.

Referring to FIG. 4, the transducer device 10 may also include a coupling membrane, such as an inflatable bag or balloon 150. The balloon 150 includes a proximal end 152, a distal end 154, and an interior 156 within which the first and/or second elongate members 102, 104 may be disposed. The proximal end 152 of the balloon 150 has an opening 157 communicating with the interior 156 for delivering fluid therein. The balloon 150 may be expandable from a collapsed configuration to facilitate insertion into a body passage to an expanded configuration for substantially engaging tissue surrounding the body passage when fluid 158 is introduced into the interior 156. The balloon 150 may be substantially inelastic, i.e., may be folded or otherwise compressed into the collapsed configuration, and may be expanded to a predetermined size as fluid is introduced into the interior 156. Alternatively, the balloon 150 may be elastic and/or compliant such that the balloon 150 may expand to fill the available volume and may substantially conform to the shape of the wall and tissue surrounding the body passage.

The fluid 158 may be a liquid acoustic propagation medium for propagating or transmitting acoustic energy generated by the transducer array 118. The balloon 150 and/or fluid 158 preferably have an acoustic impedance that corresponds substantially to the acoustic impedance of tissue. For example, the balloon 150 may be made from a polymer or rubber, such as EPDM rubber, and the fluid 158 may be degassed water.

Figure 5:
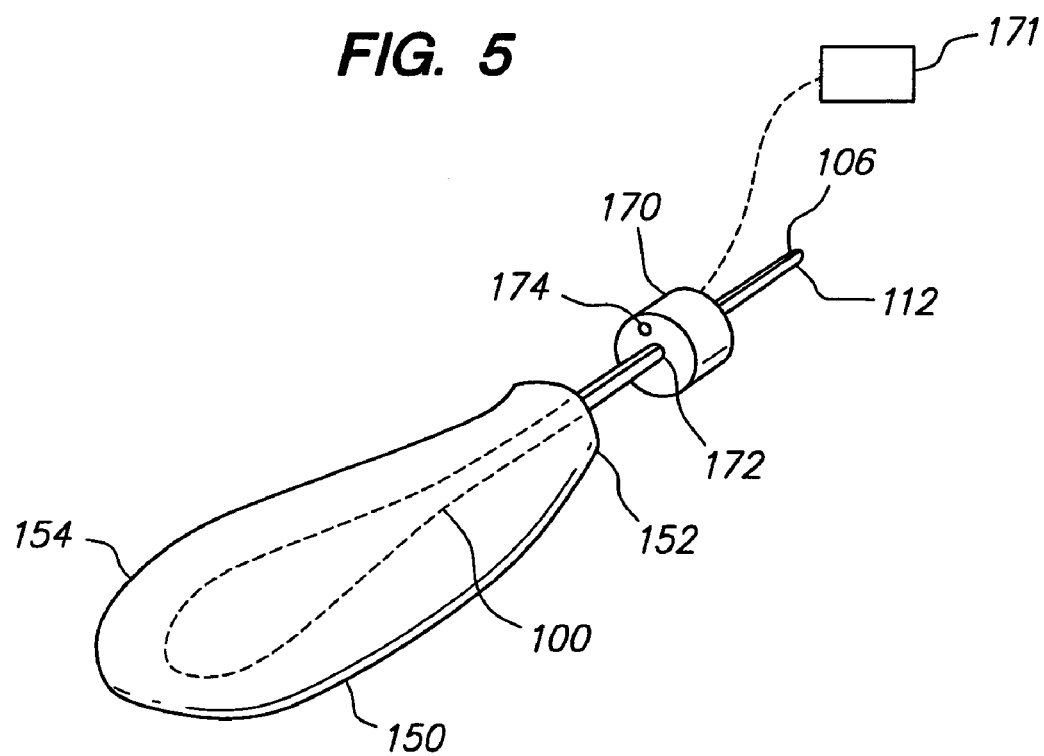
FIG. 5 is a perspective view of the transducer device of FIG. 4, showing a plug for sealing an inlet of the balloon and a source of inflation fluid coupled to the plug.

As shown in FIG. 5, the transducer device 100 may include a coupler or plug 170 that may be received in the opening 157 or otherwise secured to the proximal end 152 of the balloon 150. The plug 170 may include an adapter (not shown) for coupling the proximal end 152 of the balloon 150 to a source of fluid 171. In the illustrated embodiment, the plug 170 is an annular body including an opening 172 through which the proximal ends 106, 112 of the elongate members 102, 104 may be received. The plug 170, as shown, has a circular cross-sectional shape, although the plug 170 may have other cross-sectional shapes, such as an elliptical shape, a rectangle shape, or other desired shapes. The plug 170 preferably has a shape for mating with the proximal end 152 of the balloon 150, or the plug 170 and/or proximal end 152 may include connector(s) for securing the plug 170 to the balloon 150.

The plug 170 may include a port 174 extending therethrough for delivering and/or draining fluid 158 within the balloon 150. Alternatively, the plug 170 may include a separate inlet port (not shown) for delivering fluid 158 to the interior 156 of the balloon 150, and an outlet port (also not shown) for draining fluid 158 from the interior 156 of the balloon 150. Thus, delivery tube(s) (not shown) may be connected to the port(s) that may be connected to a source of fluid or a source of vacuum, e.g., a syringe and the like (not shown).

Figure 9A:
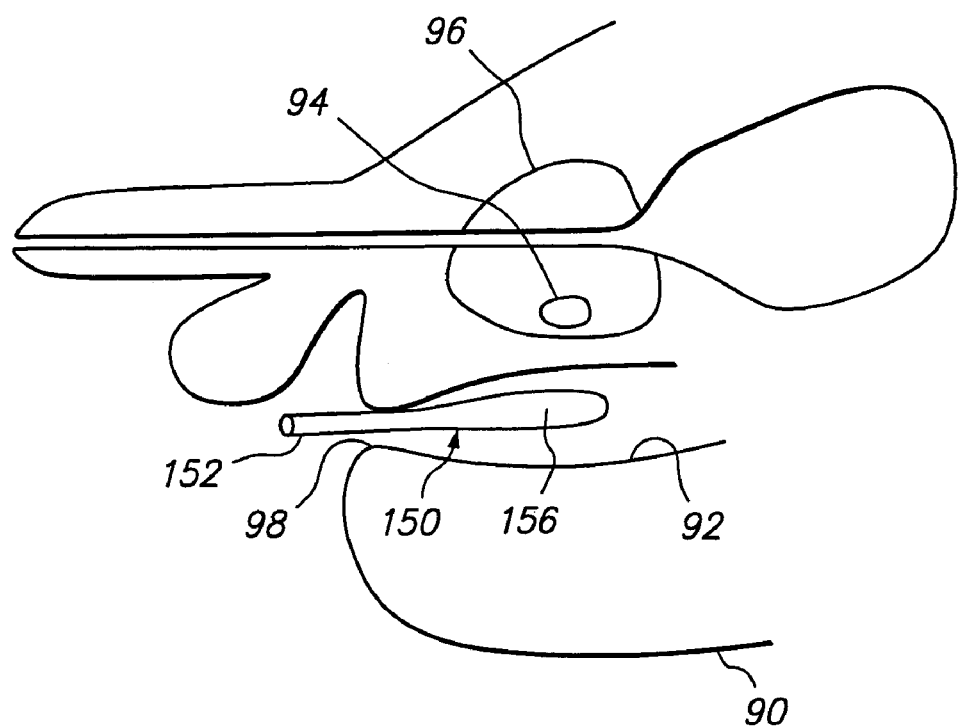
FIGS. 9A-9D are cross-sectional views of a body passage, showing a method for treating tissue adjacent the body passage using a transducer device introduced into the body passage.
Figure 9B:
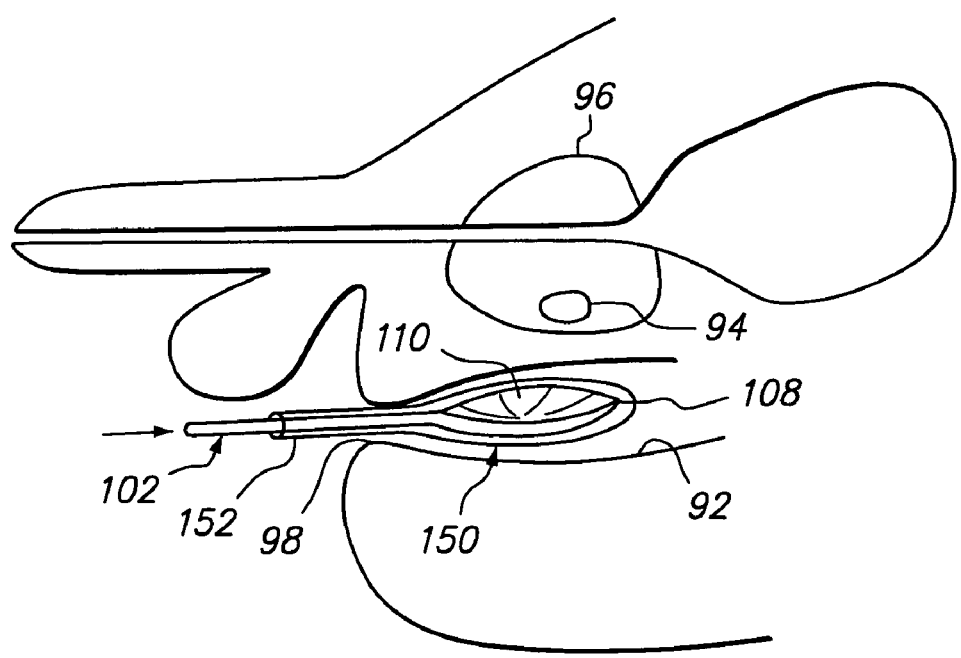
Figure 9C:
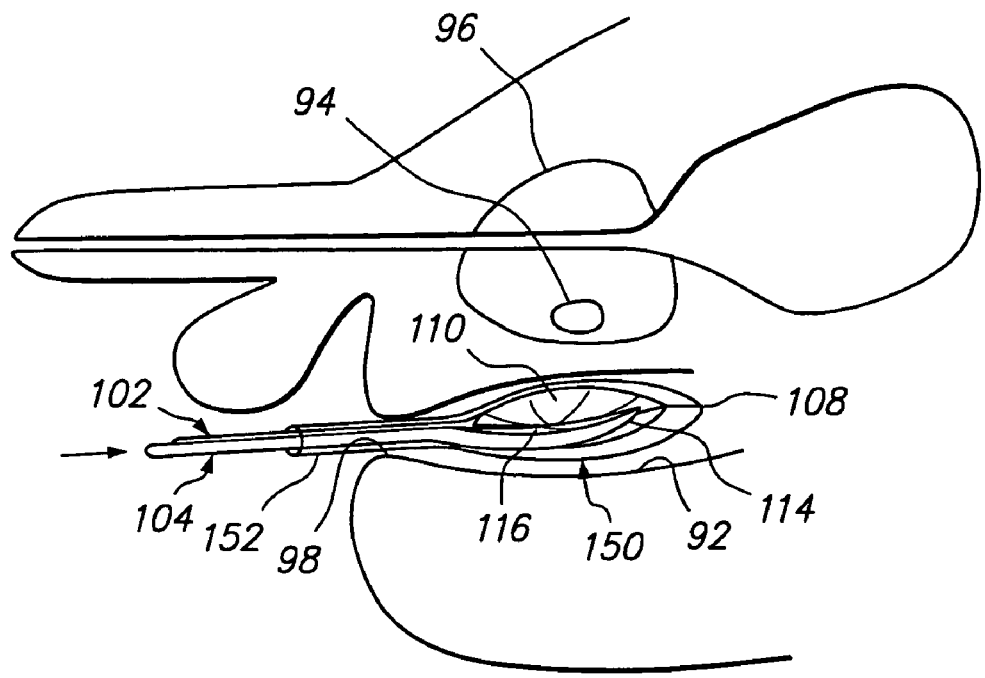

Turning to FIGS. 9A-9C, the transducer device 10 may be used to treat a target tissue region adjacent to a body passage. For example, the target tissue region may be a region 94 within a prostate 96, and the body passage may be a rectum or colon 92. As explained above, the transducer device 10 may be used to treat other target tissue regions, such as benign or malignant tumors, within organs or other tissue structures, that is located adjacent a body passage, which may be a natural passage or one surgically-created to provide access.

First, as shown in FIG. 9A, if the transducer device 10 includes a balloon 150, the balloon 150 may be inserted into the rectum 92 through rectal orifice 98. Initially, the balloon 150 may be provided in a collapsed condition, e.g., disposed within a lumen of a tubular delivery device (not shown), and advanced into the rectum 92 through the rectal orifice 98. For example, a distal end of the tubular device may be inserted first into the rectum 92, and then the balloon 150 may be inserted through the lumen of the tubular device. In addition or alternatively, the balloon 150 may be carried on an introducer that may be inserted through the proximal end 152 into the interior 156 of the balloon 150 before the balloon 150 is inserted through into the rectum 92. The balloon 150 may be collapsed around the introducer and then advanced into the lumen of the tubular device. Alternatively, the balloon 150 carried on the introducer may be inserted directly into the rectum without the tubular device. In a further alternative, the balloon 150 may be sufficiently rigid that it may be advanced through the lumen of the delivery device without an introducer. The delivery device and/or introducer may be removed from the rectum 92 once the balloon 150 is positioned adjacent the target tissue region 94. To facilitate their removal, fluid may be introduced into the interior 156 of the balloon 150 to separate the balloon 150 from the introducer.

Next, as shown in FIG. 9B, the distal end 108 of the first elongate member 102 may be inserted through the rectal orifice 98 into the rectum 92, preferably through the proximal opening 152 in the balloon 150 such that the distal end 108 enters the interior 156 of the balloon 150. Because of the width of the distal end 108, the rectal orifice 98 may be partially dilated to facilitate its insertion. However, because the distal end 108 is substantially smaller than the overall size of the assembled transducer array 118 (see FIG. 9D), risk of damaging the rectal orifice 98 is substantially reduced during insertion of the first structure 102.

Similarly, as shown in FIG. 9C, the distal end 114 of the second elongate member 104 may be inserted through the rectal orifice 98 into the rectum 92, e.g., into the interior 156 of the balloon 150. The proximal end 106 of the first elongate member 102 already occupies a portion of the rectal orifice 98, and so the distal end 114 of the second elongate member 104 must be introduced adjacent to the first elongate member 102. The relative configuration, e.g., widths or cross-sectional dimensions, of the distal ends 108, 114 may be sized to dictate the order in which the elongate members 102, 104 are inserted into the rectum 92, as will be appreciated by those skilled in the art. Generally, because the distal end 114 of the second elongate member 104 also has a cross-section sufficiently small to allow insertion of the distal end 114 through a rectal orifice 98, injury to the rectal orifice 98 is substantially reduced.

Figure 9D:
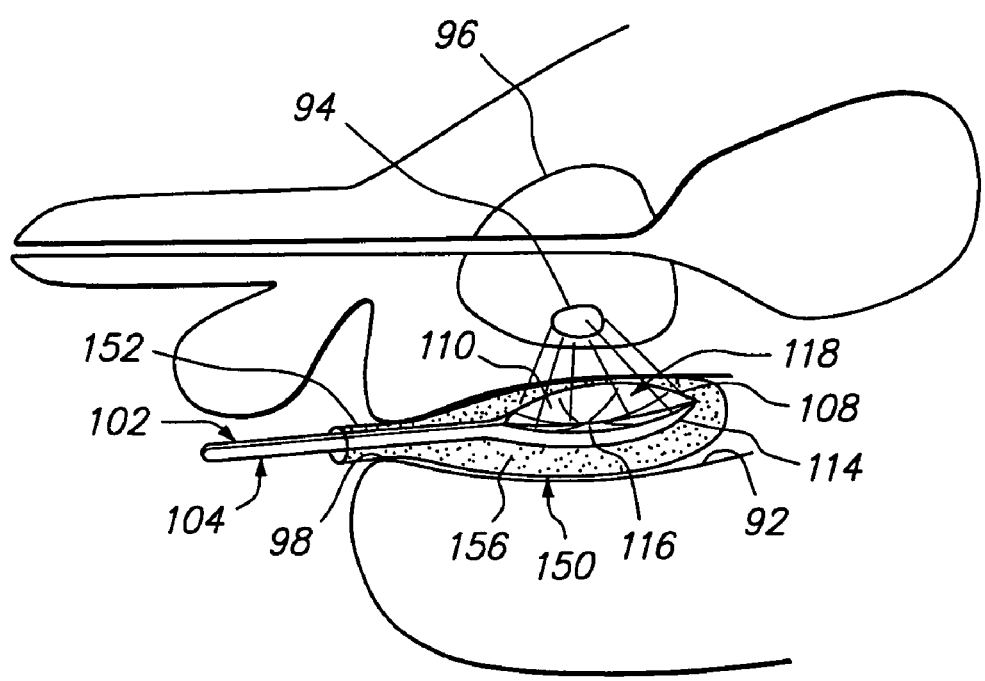

Turning to FIG. 9D, once the distal ends 108, 114 have been inserted into the rectum 92, the distal ends 108, 114 and/or the balloon 150 may be positioned to orient the transducer elements 110, 116 relative to the target region 94. In an alternative embodiment, the balloon 150 may be provided around the distal end 108 of the first elongate member 102 initially collapsed, and introduced simultaneously with the first elongate member 102.

The first and second elongate members 102, 104 may be secured together, e.g., using the cooperating hook 120 and slot 122 (not shown, see FIG. 2), to ensure that the transducer elements 110, 116 are arranged adjacent to one another to define the assembled transducer array 118. Alternatively, the first elongate member 102 may include an elongate track or rail (not shown) along which the second elongate member 104 may be advanced when inserted into the rectum 92 to dispose the transducer element(s) 116 adjacent the transducer element(s) 110. Thus, the resulting transducer array 118 may have an overall cross-sectional dimension that may be maximized relative to the narrow rectal orifice 98, i.e., that exceeds the size of single-piece transducer array that may be inserted through the rectal orifice 98. In a further alternative, the elongate members 102, 104 may remain free from one another, i.e., not connected, while the transducer elements 110, 116 may disposed adjacent one another. In this embodiment, one or both elongate members 102, 104 may carry a tracking device for monitoring their location relative to one another and/or the target tissue region 94.

If the transducer device 10 includes the balloon 150, the plug 170 (not shown, see FIG. 5) may be connected to the proximal end 152 of the balloon 150, and a source of fluid 171 (also not shown, see FIG. 5) may be coupled to the plug 170 for delivering fluid into the balloon 150. The plug 170 may be advanced over the proximal ends 106, 112 of the elongate members 102, 104, i.e., with the proximal ends 106, 112 passing through the opening 172. The plug 170 may slidably and sealingly engage the elongate members 102, 104 to prevent substantial leakage of fluid through the opening 172. Optionally, the plug 170 may sufficiently stabilize the distal ends 108, 114 of the elongate members 102, 104 that no other connectors or locking mechanism may be necessary.

As shown in FIG. 9D, fluid may be introduced into the interior 156 of the balloon 150 to expand the balloon 150 until it substantially engages the wall of the rectum 92. Preferably, the balloon 150 substantially conforms to the shape of the wall of the rectum 92 to minimize gaps and enhance acoustically coupling the transducer array 118 to tissue surrounding the rectum 92. After a desired amount of fluid has been delivered, the port 174 of the plug 170 (not shown) may be closed to prevent fluid from escaping from the interior 156 of the balloon 150. Alternatively, if the transducer device 10 does not include the plug 170, tubing (not shown) may be inserted into the proximal end 152 of the balloon 150 that is coupled to a source of fluid for inflating the balloon 150, whereupon the proximal end 152 of the balloon 150 may be sealed, e.g., using a clip, cap, and the like (not shown).

The transducer array 118 may be oriented towards the target tissue region 94, i.e., within the prostate 96, which may require the proximal ends 106, 112 of the elongate members 102, 104 to be positioned or manipulated further. Positioning the transducer array 118 may be monitored using imaging techniques known in the art, such as fluoroscopy and ultrasonic imaging. Radiopaque markers (not shown) may be provided on one or both of the distal ends 108, 114 of the elongate members 102, 104 to assist monitoring and positioning the transducer array 118.

Once the transducer 118 is properly oriented, the transducer array 118 is then activated to deliver acoustic energy to the target tissue region 94. The driver 16 and/or controller 18 (not shown, see FIG. 1) may control the acoustic energy emitted by the transducer array 118 to focus and/or adjust the intensity of the acoustic energy to heat the target tissue region 94, while minimizing heating tissue surrounding the target tissue region 94. The fluid-filled balloon 150 may enhance acoustic coupling of the transducer array 118 with the intervening tissue between the rectum 92 and the target tissue region 94, as explained above.

If the first and second elongate members 102, 104 are not connected to one another, they may be manipulated individually or together. In addition, each transducer element 110, 116 may be tested, e.g., activated individually using relatively low power, to confirm that each transducer element 110, 116 is oriented towards the target tissue region 94 before activating the entire transducer array to treat the target tissue region 94. If the focal zone of each transducer element 110, 116 is not properly focused at the target tissue region 94, the focal zone may be adjusted physically and/or electronically, as will be appreciated by those skilled in the art. Thus, the transducer elements may be provided at different positions and/or angles relative to one another before the transducer array is activated to treat the target tissue region 94. In further alternatives, transducers may be introduced into different body passages and positioned and/or focused towards a target tissue region adjacent to each of the transducers.

After a desired amount of acoustic energy has been delivered, e.g., to ablate or otherwise treat the target tissue region 94, optionally, the transducer device 10 may be moved to another location, electronically steered, and/or otherwise repositioned within the rectum 92, e.g., with the elongate members 102, 104 and/or balloon 150 remaining assembled together. Additional tissue regions may then be treated. Alternatively or finally, the transducer device 10 may be removed from the rectum 92 via the rectal orifice 98. Generally, this involves deflating the balloon 150, disconnecting the elongate members 102, 104 (if secured together), and removing the elongate members 102, 104 one at a time. The balloon 150 may be removed with the final elongate member or after all of the elongate members are removed from the rectum 92.

Figure 6:
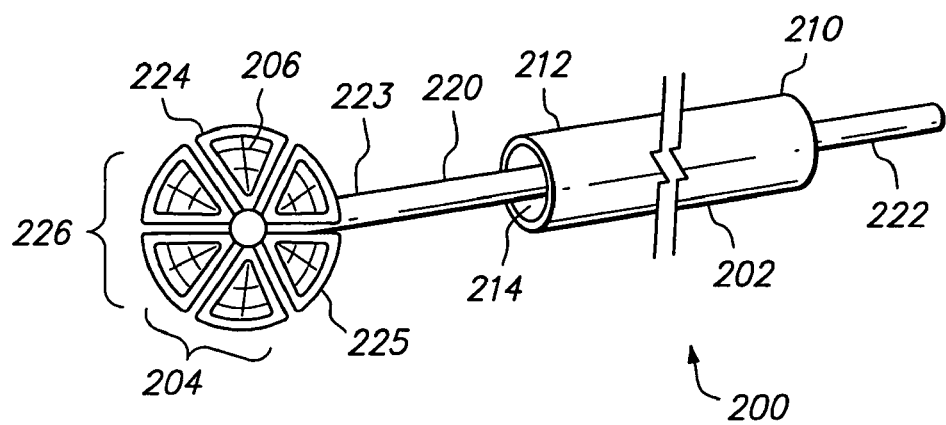
FIGS. 6 and 7 are perspective views of another embodiment of a transducer device, including an expandable structure carrying a plurality of transducer elements in enlarged and contracted configurations, respectively.
Figure 7:
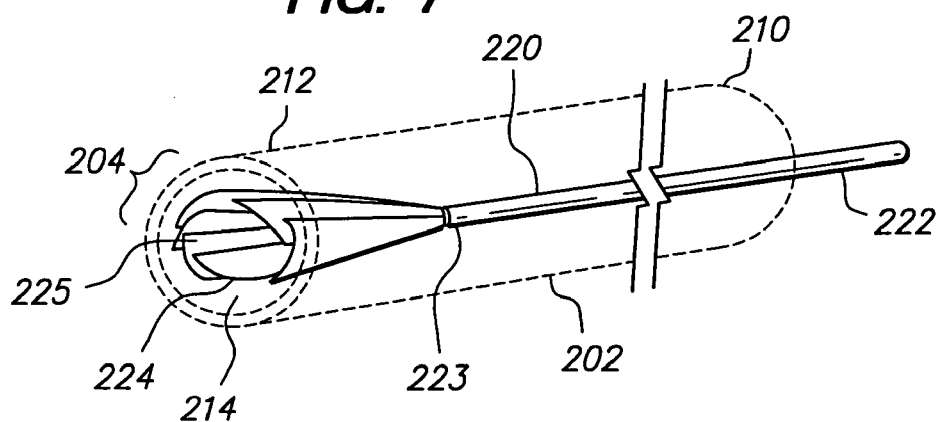
Figure 8:
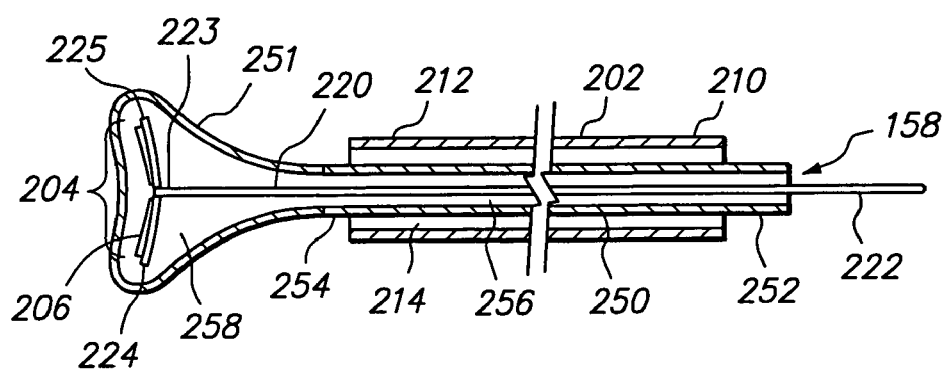
FIG. 8 is a cross-sectional side view of the transducer device of FIGS. 6 and 7, including an expandable balloon surrounding the expandable structure.

Turning to FIGS. 6-8, another embodiment of a transducer device 200 is shown that includes a tubular delivery device 202, and an elongate member 220 carrying a plurality of transducer elements 206. The tubular delivery device 202 has a proximal end 210, a distal end 212, and a lumen 214 extending between the proximal and distal ends 210, 212. The elongate member 220 includes a proximal end 222, a distal end 223, and an expandable structure 224 on the distal end 223 that carries the transducer elements 206. Optionally, the transducer device 200 may also include a balloon, bag, or other coupling membrane 251 (shown in FIG. 8) and a coupler or plug (not shown) for sealing the balloon 251 and/or coupling a source of fluid to the balloon 251 medium, similar to the embodiments described previously with reference to FIGS. 4 and 5

The expandable structure 224 may be bent, folded, or otherwise collapsed into a low profile or contracted configuration (shown in FIG. 7), e.g., to facilitate advancing or retracting the expandable structure 224 out of and into the lumen 214 of the delivery device 202. The structure 224 is also expandable to an enlarged configured (shown in FIG. 6) for arranging the transducer elements 206 to define a transducer array 220. The elongate member 222 may be a substantially rigid, semi-rigid, or flexible wire or other body and the expandable structure 224 may be attached to or otherwise carried by the distal end 223.

The expandable structure 234 may be made from an elastic material, such as plastic and/or metal, e.g., biased to expand towards the enlarged configuration, yet elastically deformable towards the contracted configuration. In a preferred embodiment, the expandable structure 224 may be formed from a super-elastic alloys, such as a nickel/titanium ("Nitinol") alloy. Other materials known in the art may also be used so long as the expandable structure 224 is capable of performing the functions described herein.

The expandable structure 224, elongate member 220, and/or delivery device 202 may include one or more radiopaque markers (not shown) to assisting monitoring the transducer device 200 as it being manipulated within a body passage of a patient. For example, the expandable structure 224 may be coated or mixed with radiopaque materials, such as tantalum, gold, tungsten or platinum, barium sulfate, bismuth oxide, bismuth subcarbonate, and the like. Alternatively, continuous or discrete radiopaque markers may be affixed to the expandable structure 224. In a further alternative, one or more of the components may include microcoil trackers that may be compatible for monitoring using MRI.

In the exemplary embodiment shown in FIGS. 6 and 7, the expandable structure 224 may include a plurality of petals 225, each carrying one or more transducer elements 206. The petals 225 may be connected to the distal end 223 of the elongate member 220 by respective hinged regions, which may be living hinges, pinned hinges, and the like. The petals 224 may be biased to assume the enlarged configuration automatically when deployed from the lumen 214 of the delivery device 202, but may be compressed into the contracted configuration simply by retracting the distal end 223 of the elongate member 220 into the lumen 214. Alternatively, the petals 225 may be coupled to wires or other elements (not shown) that may be manipulated to expand and/or contract the petal s 225. The number of petals 224 may vary, e.g., four, five, six (as shown), or more, and should not limited to the illustrated embodiment.

Each of the transducer elements 206 may include a single piezoceramic element or preferably may include a mosaic arrangement including a plurality of small piezoceramic elements. The piezoceramic elements may have a variety of geometric shapes, such as hexagons, triangles, squares, and the like.

Similar to the previous embodiments, a driver 16 and/or driver 18 (not shown, see FIG. 1) may be coupled to the transducer elements 206, e.g., by leads (not shown) on or in the elongate member 220. The transducer elements 206 may be driven with respective drive signals for focusing acoustic energy transmitted by the transducer elements 206 towards a focal zone within a target region. Phase, amplitude, and/or other parameters of the drive signals may be controlled to provide a desired size, shape, and/or location for the focal zone, similar to the previous embodiment.

In the enlarged configuration shown in FIG. 6, the resulting transducer array 226 may have a variety of shapes and configurations. In one embodiment, the transducer array 226 may have a concave or bowl shape, such as a "spherical cap" shape, i.e., having a substantially constant radius of curvature such that the transducer array 226 has an inside surface defining a portion of a sphere. Alternatively, the transducer array 226 may have a substantially flat configuration (not shown), and/or may include an outer perimeter that is generally, but not necessarily, circular (not shown). The transducer array 226 may be divided into any desired number of rings and/or sectors (not shown), all similar to the previous embodiment.

Those skilled in the art will appreciate that the expandable structure 224 may include other elements that may be collapsed and/or expanded. For example, in an alternative embodiment, the expandable structure may include an inflatable balloon (not shown) carrying a plurality of transducer elements. As the balloon is inflated, the transducer elements may assume a configuration of a transducer array, similar to the previous embodiment. In a further alternative embodiment, the structure 204 may include other hinged elements that are connected to otherwise carried by the distal end 223 of the elongate member 220.

As shown in FIG. 8, the expandable structure 224 is expanded towards the enlarged configuration within a balloon 251. The transducer device 200 also may include a tubular element 250, including a proximal end 252, a distal end 254, and a lumen 256 extending between the proximal and distal ends 252, 254. The tubular element 250 may be positioned within the lumen 214 of the delivery device 202, and surround the elongate member 220.

The balloon 251 may be coupled to the distal end 254 of the tubular element 250 such that an interior 258 of the balloon 251 communicates with the lumen 256 of the tubular element 250. The balloon 251 is expandable, similar to the previous embodiment, towards an expanded configuration that is larger than the expandable structure 224 in its enlarged configuration, e.g., to substantially engage a wall of a body passage within which the transducer device 200 is introduced. The balloon 251 may a collapsed configuration or low profile when deflated and disposed within the lumen 214 of the delivery device 202, and may be inflated towards the expanded configuration. The balloon 251 is preferably made from a material including an acoustic impedance that is substantially similar to the acoustic impedance of body tissue, as discussed previously with reference to the balloon 150.

When using the ultrasound device 200 to treat a prostate, the tubular delivery device 202 is first inserted into a rectum through a rectal orifice (not shown). The expandable structure 224 may be placed within the lumen 214 of the delivery device 202 before or after the tubular delivery device 202 is inserted into the rectum. If the transducer device 200 includes a balloon 251, the balloon 251, together with the elongate member 220, may be introduced into the lumen 214 of the delivery device 202 before or after the delivery device 202 is inserted into the rectum.

After the distal end 212 of the delivery device 202 has been advanced sufficiently, the distal end of the elongate member 220 may be advanced from the delivery device to deploy the expandable structure 224 within the rectum. The expandable structure 204 may be manipulated within the rectum until the petals 225 are fully exposed, whereupon the petals 225 may automatically expand or may be actuated to expand towards the enlarged configuration. In the enlarged configuration, the transducer elements 206 generally assume a transducer array 226, which may then be oriented towards a target tissue region (not shown).

If the transducer device 200 includes a balloon 251, the balloon 251 maybe advanced into the rectum before or simultaneously with the elongate member 220. Other methods known in the art may also be used to deploy the balloon 251. For example, a plunger or guidewire (not shown) may be used to deliver the balloon 251 into the rectum.

After the balloon 251 and the expandable structure 204 have been deployed and desirably placed within the rectum, fluid may be delivered into the interior 258 of the balloon 251 to expand the balloon 251 until it substantially engages the surrounding wall of the rectum. Fluid may be delivered directly into the open proximal end 252 of the tubular element 250 and into the interior 258 of the balloon 251. Alternatively, a coupler or plug (not shown), similar to that described previously with reference to FIG. 5, may be used to seal the balloon 251 and/or couple the balloon 251 to a source of fluid.

Once the transducer array 226 is properly positioned and/or oriented, drive signals may be delivered to the transducer elements 206 to focus acoustic energy to the target site, similar to the previous embodiment. After sufficient ultrasonic energy has been delivered, the expandable structure 224 (and balloon 251) may be collapsed, repositioned, expanded and activated to focus acoustic energy at a an other target site. Once sufficient tissue is treated, the expandable structure 224 (and balloon 251) may be withdrawn into the lumen 214 of the delivery device 202 and/or otherwise removed from the rectum.

Although the above described embodiments have been described with reference to treating a prostate, it should be understood by those skilled in the art that the apparatus and methods described herein may also be used to treat other areas of a body. In addition, the transducer devices described herein may be used in cooperation with external transducer arrays, such as those described in the references incorporated by reference elsewhere herein. Thus, a hybrid procedure, in which acoustic energy is delivered to a target site using two transducers, one internal and one external, simultaneously. Alternatively, multiple transducer devices, such as those described herein, may be inserted into different body passages for delivering acoustic energy to a target site in cooperation within one another. For example, in a single treatment, a first transducer device may be introduced into a rectum, and a second transducer device may be introduced into a vagina of a female patient to treat tissue adjacent the rectum and the vagina. Furthermore, besides treating tissue, the transducer devices described herein may also be for obtaining acoustic images of tissue regions within a patient.

Thus, although several preferred embodiments have been shown and described, it would be apparent to those skilled in the art that many changes and modifications may be made thereunto without departing from the scope of the invention, which is defined by the following claims and their equivalents.

What is claimed:

1. A method for delivering acoustic energy into a target tissue region adjacent a body passage, the method comprising: introducing a first member into the body passage until a first transducer carried by the first member is disposed adjacent the target tissue region; introducing a second member into the body passage until a second transducer carried by the second member is disposed adjacent the first transducer; detachably coupling the first and the second transducers to each other to at least partially form a transducer array; and delivering acoustic energy from the first and second transducers towards the target tissue region to treat tissue therein.

2. The method of claim 1, further comprising securing the first member to the second member to substantially maintain the first and second transducers relative to one another.

3. The method of claim 1, further comprising introducing an expandable member into the body passage; introducing the first and the second transducers within am interior or the expandable member; and expanding the expandable member until it substantially engages a wall of the body passage.

4. The method of claim 3, wherein fluid is delivered into the interior of the expandable member to expand the expandable member until it substantially engages a wall of the body passage, the fluid acoustically coupling the first and second transducers with the wall of the body passage.

5. The method of claim 1, wherein at least one of the first and second transducers comprises a plurality or transducer elements, and wherein acoustic energy is delivered from the plurality of transducer elements towards the target region to treat tissue therein.

6. The method of claim 1, further comprising introducing a third member into the body passage until a third transducer carried by the third member is disposed adjacent the first and second transducer elements, and wherein acoustic energy is delivered from the third transducer towards the target region in conjunction with the first and second transducers.

7. The method of claim 1, wherein the body passage comprises a natural body lumen.

8. The method of claim 1, further comprising creating the body passage through tissue to a location adjacent the target tissue region.

9. Apparatus for treating internal body tissue, comprising:
a first elongate member sized and shaped for insertion into a body passage, and including a first transducer carried on a distal end of the first member distal end;
a second elongate member sized and shaped for insertion into a body passage, and including a second transducer carried on a distal end of the second member; and
a controller operatively connected to the first and second transducers,
wherein the first and second members are configured for separate insertion into a same or differing body passage, whereby the first and second transducers may form respective active transducer elements of an array coordinated by the controller to deliver focused acoustic energy to treat tissue in a target tissue region located adjacent the respective same or differing body passages.

10. The apparatus of claim 9, further comprising one or more additional elongate members, each having a distal end sized and shaped for insertion into a body passage, and each carrying an additional transducer on its distal end, wherein the one or more additional members are each configured for separate insertion into a same or differing body passage as the first and second members, such that the transducers carried by the one or more additional members are a part of the transducer array.

11. The apparatus of claim 9, further comprising a connector for substantially securing the first and second members relative to one another.

12. The apparatus of claim 11, wherein the connector comprises one or more cooperating hooks and openings on the first and second elongate members.

13. The apparatus of claim 9, the first and second members each comprising one or more leads extending from the respective first and second transducers for coupling the first and second transducer elements to at least one of a driver and a controller.

14. The apparatus of claim 9, further expanding an expandable member comprising an interior within which the respective first and second member distal ends may be positioned, and an inlet communicating with the interior for introducing fluid into the interior, that expandable member being expandable from a collapsed configuration to facilitate insertion into a body passage to an enlarged configuration for substantially engaging tissue surrounding the body passage when fluid is introduced into the interior.

15. The apparatus of claim 14, further comprising a source of fluid coupled to the inlet for delivering fluid into the interior of the expandable member.

16. The apparatus of claim 14, wherein the expandable member comprises a material having an acoustic impedance that corresponding substantially to an acoustic impedance of the surrounding tissue.

17. The apparatus of claim 9, wherein the traducer array has a cross section between about ten and seventy millimeters (10-70 mm).

18. The apparatus of claim 9, wherein the first and second elongate members each carries a plurality of transducer elements on its respective distal end.

19. A method for treating internal body tissue, comprising:

introducing a first elongate member into a body passage, the first elongate member carrying one at more transducer elements operatively connected to a controller;

introducing a second elongate member into a same or different body passage, the second elongate member carrying one or more additional transducer elements operatively connected to the controller; and simultaneously delivering acoustic energy, coordinated by the controller, from at least one transducer element carried on the first elongate member and from at least one transducer element carried an the second elongate member towards a target tissue region to treat tissue therein.

20. The method of claim 19, further comprising tracking a relative position of the respective transducer elements carried on the first and second elongate members.

21. The method of claim 19, wherein the first and second elongate members are introduced into the same body passage.

22. The method of claim 19, wherein the first elongate member is introduced into a first body passage, and the second elongate member is introduced into a second body passage.

* * * * *